United States Patent [19]
Yamada et al.

[11] Patent Number: 5,145,775
[45] Date of Patent: Sep. 8, 1992

[54] POLYHEDRIN GENE AND GENETIC ENGINEERING THEREOF

[75] Inventors: Nobutoshi Yamada; Norifusa Matsuo; Takaaki Araki, all of Kusatsu, Japan

[73] Assignee: Research Association for Biotechnology of Agricultural Chemicals, Tokyo, Japan

[21] Appl. No.: 483,823

[22] Filed: Feb. 23, 1990

[30] Foreign Application Priority Data

Feb. 28, 1989 [JP] Japan .................................. 1-46736

[51] Int. Cl.$^5$ ...................... C12P 21/02; C12N 15/34; C12N 15/86; C12N 15/00
[52] U.S. Cl. ................. 435/69.1; 435/412.3; 435/320.7; 435/240.1; 537/27
[58] Field of Search ............ 536/27; 435/320.1, 172.3, 435/69.1, 240.2

[56] References Cited

U.S. PATENT DOCUMENTS 4,745,051  5/1988  Smith et al. .................. 435/172.1 X

FOREIGN PATENT DOCUMENTS 0127839 12/1984 European Pat. Off. .
0175852  4/1986 European Pat. Off. .
 222412  5/1987 European Pat. Off. .
0272858  6/1988 European Pat. Off. .
8802030  3/1988 PCT Int'l Appl. .
8807082  9/1988 PCT Int'l Appl. .

OTHER PUBLICATIONS

Gonzalez et al., Virology 170:160–175 (1989).
Smith et al., Virology 123:2393–2406 (1982).
Journal of Virology vol. 54, No. 2, May 1985, pp. 436–445, Baltimore, U.S.; K. Iatrou et al.: "Polyhedrin Gene of Bombyx mori Nuclear Polyhedrosis Virus".
Virology vol. 131, No. 2, Dec. 1983, pp. 561–565, N.Y., U.S.; B. J. L. Hooft Van Iddekinge et al.: "Nucleotide Sequence of the Polyhedrin Gene of Autographa californica Nuclear Polyhedrosis Virus".
Chemical Abstracts vol. 99, No. 19, Nov. 7, 1983, p. 314, abstract No. 154864r, Columbus, Ohio, U.S.; M. V. Ashok et al.: "Centain observations on the physico-chemical properties of nuclear polyhedrosis virus of Spodoptera litura (Fabricius)".
J. Entomol. Res. 1981, vol. 5, No. 1, pp. 43–46.
Chemical Abstracts vol. 83, No. 15, Oct. 13, 1975, p. 249, Abstract No. 128489x, Columbus, Ohio, U.S.; V. M. Pawar et al.: "Amino acid and nucleic acid composition of the polyhedral inclusion bodies of the nuclear polyhedrosis virus of Spodoptera litura".
Curr. Sci. 1975, vol. 44, No. 13, pp. 475, 476.
J. Gen. Virology vol. 67, 1986, pp. 1073–1079, Colchester, GB; D. Leisy et al.: "Location and Nucleotide Sequence of the Orgyia pseudotsugata Single Nucleocapsid Nuclear Polyedrosis Virsu Polyhedrin Gene".
Maniatis et al., Molecular Cloning Laboratory Manual, Cold Spring Laboratory, pp. 10–15 (1982).

Primary Examiner—Richard A. Schwartz
Assistant Examiner—S. L. Nolan
Attorney, Agent, or Firm—Oblon, Spivak, McClelland, Maier & Neustadt

[57] ABSTRACT

A polyhedrin gene of *Spodoptera litura* nuclear polyhedrosis virus (SlNPV C-411) has the following restriction enzyme cleavage map and about 3 kilobase pairs:

At least a part of said polyhedrin gene can be substituted by a gene coding for a useful substance to construct a vector and a recombinant virus, and it is possible to produce a useful substance such as a peptide, protein or glycoprotein by culturing a cell infected with the recombinant virus.

16 Claims, 11 Drawing Sheets

FIG. 1

```
GATAAAATTTTAAAATTTTAATCTATAGATAGAAAGATAAAATTTTAATCTATAGATAAA    60

AGTAAAGTATTTAGATAAAATTTTATCTAAAAATTTTAATCTAAAGATAAAATATTGACA   120
                                  S⎯→
TGCGATTTCTCAATACCAATGAAGATCAAGTGATGATAAGGAATTTATTACTATCGTTCT   180
                          M  Y  S  R  Y  S  A  Y  N  Y  S     11
AGATAGTGAAAAATCAAATATCCCATAATGTATAGTCGCTACAGTGCCTACAATTATAGT   240
 P  H  L  G  K  T  Y  V  V  Y  D  N  K  Y  Y  K  N  L  G  H  V   31
CCCCATCTGGGCAAAACCTATGTATACGATAACAAGTATTACAAAAATTTAGGTCACGTG   300
 I  K  N  A  K  R  K  H  D  A  L  E  R  E  A  D  E  R  E  L    51
ATCAAAAATGCTAAGCGCAAACACGATGCTCTCGAACGCGAGGCCGACGAGCGCGAGCTC   360
 D  H  L  D  K  Y  L  V  A  E  D  P  F  M  G  P  G  K  N  Q    71
GATCACCTAGACAAGTATCTAGTCGCCGAAGATCCGTTCATGGGTCCCGGTAAAAATCAA   420
 K  L  T  L  F  K  E  I  R  N  V  K  P  D  T  M  K  L  I  V    91
AAGTTGACTCTGTTCAAGGAGATCCGTAACGTGAAACCCGACACGATGAAGCTGATCGTC   480
 N  W  N  G  K  E  F  L  R  E  T  W  T  R  F  M  E  D  S  F   111
AACTGGAACGGCAAAGAGTTTCTCCGTGAGACTTGGAGCCGTTTCATGGAAGACAGCTTC   540
 P  I  V  N  D  Q  E  V  M  D  V  F  L  V  V  N  M  R  P  T   131
CCCATCGTGAACGATCAAGAAGTGATGGACGTGTTTCTAGTGGTGAACATGCGTCCCACT   600
 R  P  N  R  C  F  R  F  L  A  Q  H  A  L  R  C  D  P  E  Y   151
AGACCGAACCGTTGCTTTAGATTTTTGGCGCAACACGCGCTCCGATGCGACCCCGAGTAC   660
 V  P  H  D  V  I  R  I  V  E  P  S  Y  V  G  T  N  N  E  Y   171
GTTCCCCACGACGTGATCCGCATCGTCGAACCGTCGTACGTCGGCACCAACAATGAATAC   720
 R  I  S  L  A  K  K  G  G  C  P  V  M  N  L  H  A  E  Y    191
CGCATCAGTCTCGCCAAGAAAGGTGGCGGTTGTCCCGTGATGAACCTGCACGCCGAATAC   780
 T  T  S  F  E  S  F  I  D  K  V  I  W  Y  N  F  Y  K  P  I   211
ACCACTTCGTTTGAGAGTTTCATCGACAAGGTGATATGGTACAACTTTTACAAGCCCATC   840
 V  Y  V  G  T  D  S  A  E  E  E  E  I  L  L  E  V  S  L  V   231
GTGTACGTGGGCACCGATTCGGCCGAAGAGGAGGAGATCCTTCTCGAAGTGTCGCTCGTG   900
 F  K  I  K  E  F  A  P  D  A  P  L  Y  T  G  P  A  Y
TTCAAGATCAAAGAGTTTGCTCCCGACGCGCCACTCTACACCGGTCCCGCGTACTAAATT   960

TGCGAAGAGGACAGTCGAGCCAGTTCGTCGACTCTCCGTTTGAGCTGTGCAATTTTTTCG  1020

TCGTCTTTGTCGTCGCGACGCTTCTGAAGCATACTTTTCGCCTTTGCGATGTCATCGTTT  1080

ACGATAAAGTATTCGACGGCTCGCAAAAATCTCTCTCTGGACATTGTGTCCGCTCGGTCG  1140

CCGTTTGCCGCCTCTTTGACCGCGCTCGGCTCTGCGTCTTTAAACATAAACTGAACAATA  1200

GACATCGTCCGTTCGACGCTGTCAATGAGCCGCAAAGCGTCATCTTTCGCAACGATATTT  1260
                                               T⎯→
TTTACATTGTTTAAATCTCGAAGTATATCGGCCACGTTGCTTTGTATAATTTGGCTGTTT  1320
S = TRANSCRIPTION INITIATION SITE
T = TRANSCRIPTION TERMINATION SITE              FIG. 4
```

```
        -120        -110       -100        -90        -80        -70
AcMNPV  AATGTCTATC AATATATAGT TGCTGATATC ATGGAGATAA TTAAAATGAT AACCATCTCG
BmNPV   CAATTATAAA TGTCAAATTT GTTTTTATT  AACGATACAA TGGAAATAAT AACCATCTCC
OpMNPV  CTGCTTACGA ATTTATGTAC AACAAAAAAT AAAACACTAG TTACTATTGG CGTTTCGTTT
OpSNPV  ATATTTGTGT CGATAGCGCG GGCTGAGTAA TTCGATTTTT GCGTGAGAAT TTCAACGACA

-60        -50        -40        -30        -20        -10
AcMNPV  CAAATAAATA AGTATTTTAG TGTTTCGTA  ACAGTTTGT  AATAAAAAAA CCTCTAAATA ATG
BmNPV   CAAATAAATA AGTATTTTAC TGTTTCGTA  ACAGTTTTGT AATAAAAAAA CCTATAAAT  ATG
OpMNPV  TTTATTAATA AGTAATTTCC TGTTATTGTA ACAATTTTGT AAAAAAATTT CCTATAACC  ATG
OpSNPV  CACCTCAATA AGTATTTTTG TCCTTTCGTA AAACATTGTG AAATTTCAAA TACACCATA  ATG
```

FIG. 5

POLYHEDRIN GENE AND GENETIC ENGINEERING THEREOF

BACKGROUND OF THE INVENTION

1. FIELD OF THE INVENTION

The present invention relates to a novel polyhedrin gene and genetic engineering thereof. More particularly, it relates to a novel polyhedrin gene of *Spodoptera litura* nuclear polyhedrosis virus, vectors containing a heterologous sequence of DNA which is under the control of the polyhedrin promoter, recombinant viruses containing a heterologous sequence of DNA which is under the control of the polyhedrin promoter, cells infected with such recombinant viruses, methods of producing such vectors or recombinant viruses, methods of producing polypeptides using such recombinant viruses, a recombinant gene containing at least part of the polyhedrin gene replaced with a heterologous sequence of DNA, and a fusion peptide fused to at least part of the polyhedrin peptide.

2. DISCUSSION OF BACKGROUND

It is already known to produce useful substances by gene recombinant technology by means of baculoviruses. For example, U.S. Pat. No. 4,745,051 and European Patent Publications No. 0175852 and No. 0222412 disclose the production of useful substances by recombining the polyhedrin genes of the nuclear polyhedrosis viruses of *Augrapha californica* and *Bombyx mori*, respectively hereinafter referred to simply as AcNPV and BmNPV, respectively).

However, the vectors of AcNPV and BmNPV are as long as about 10 kilobase pairs by themselves, whereby at the time of cloning a gene coding for a useful substance with such vectors, the efficiency of transformation with *Escherichia coli* is poor, and it is difficult to clone a large gene encoding for a useful substance.

Thus, there remains a need for a method for producing polypeptides free of the above-described drawback. There also remains a need for polyhedrin genes, recombinant genes, vectors, recombinant viruses and cells infected with such recombinant viruses which can be used in such a method and there is also a need for methods to produce such vectors and recombinant viruses.

SUMMARY OF THE INVENTION

Accordingly it is one object of the present invention to provide an isolated polyhedrin gene which will allow for efficient transformation when cloning a heterologous DNA sequence.

It is another object to provide vectors which contain a polyhedrin gene in which at least part of the DNA sequence encoding for the polyhedrin protein has been replaced with a heterologous DNA sequence.

It is another object of the present invention to provide vectors containing a polyhedrin promoter upstream from the 5' end of a heterologous DNA sequence and a fragment of a polyhedrin gene downstream from the 3' end of the heterologous DNA sequence.

It is another object to provide a method for producing such vectors.

It is another object to provide recombinant viruses in which at least part of the DNA sequence encoding for the polyhedrin protein has been replaced with a heterologous DNA sequence.

It is another object to provide recombinant viruses, wherein the DNA contains a polyhedrin promoter upstream from the 5' end of a heterologous DNA sequence and a fragment of a polyhedrin gene downstream from the 3' end of the heterologous DNA sequence.

It is another object to provide a method for producing such recombinant viruses.

It is another object to provide cells infected with such recombinant viruses.

It is another object to provide a method for producing a polypeptide by culturing such cells.

It is another object of the present invention to provide a recombinant gene containing a polyhedrin gene in which at least part of the DNA sequence encoding for the polyhedrin protein has been replaced with a heterologous DNA sequence.

It is another object of the present invention to provide a recombinant gene containing a polyhedrin promoter upstream from the 5' end of a heterologous DNA sequence and a fragment of a polyhedrin gene downstream from the 3' end of the heterologous DNA sequence.

It is another object of the present invention to provide a fusion protein produced by a process of culturing a cell infected with a recombinant virus, wherein the DNA contains a polyhedrin promoter upstream from the 5' end of a heterologous DNA sequence and a fragment of a polyhedrin gene downstream from the 3' end of the heterologous DNA sequence.

It is another object of the present invention to provide a fusion protein containing a polypeptide fused to at least part of the polyhedrin peptide.

These and other objects, which will become apparent during the course of the following detailed description have been achieved by the present inventors discovery of a novel polyhedrin gene from *Spodoptera litura* nuclear polyhedrosis virus (referred to simply as SlNPV, obtained from the National Agriculture Research Center, the Ministry of the Agriculture, Forestry and Fisheries of Japan) which is different from the conventional polyhedrin genes and their success in improving the conventional methods by recombining the novel polyhedrin gene.

Thus, the present invention provides:

1. An isolated polyhedrin gene of *Spodoptera litura* nuclear polyhedrosis virus (SlNPV C-411) having the following restriction enzyme cleavage map and about 3 kilobase pairs:

```
                                    HincII,
                                    AccI or
HindIII  HincII  XbaI  AccI  HincII  SalI     HindIII
   |       |      |     |     |       |         |
   |_____|_____|_____|_____|_____|_____|
```

2. An isolated polyhedrin gene of *Spodoptera litura* nuclear polyhedrosis virus (SlNPV C-411) having a DNA sequence coding for the following amino acid sequence:

|   |   |   |   |   |   |   |   |   | 10 |
|---|---|---|---|---|---|---|---|---|----|
| M | Y | S | R | Y | S | A | Y | N | Y  |
| S | P | H | L | G | K | T | Y | V | 20 Y |
| D | N | K | Y | Y | K | N | L | G | 30 H |
| V | I | K | N | A | K | R | K | H | 40 D |

| | | | | | | | | |
|---|---|---|---|---|---|---|---|---|
| A | L | E | R | E | A | D | E | R |
| | | | | | | | | 50 E |
| L | D | H | L | D | K | Y | L | V |
| | | | | | | | | 60 A |
| E | D | P | F | M | G | P | G | K |
| | | | | | | | | 70 N |
| Q | K | L | T | L | F | K | E | I |
| | | | | | | | | 80 R |
| N | V | K | P | D | T | M | K | L |
| | | | | | | | | 90 I |
| V | N | W | N | G | K | E | F | L |
| | | | | | | | | 100 R |
| E | T | W | T | R | F | M | E | D |
| | | | | | | | | 110 S |
| E | P | I | V | N | D | Q | E | V |
| | | | | | | | | 120 M |
| D | V | F | L | V | V | N | M | R |
| | | | | | | | | 130 P |
| T | R | P | N | R | C | F | R | F |
| | | | | | | | | 140 L |
| A | Q | H | A | L | R | C | D | P |
| | | | | | | | | 150 E |
| Y | V | P | H | D | V | I | R | I |
| | | | | | | | | 160 V |
| E | P | S | Y | V | G | T | N | N |
| | | | | | | | | 170 E |
| | | | | | | | | 180 |

| | | | | | | | | |
|---|---|---|---|---|---|---|---|---|
| Y | R | I | S | L | A | K | K | G |
| | | | | | | | | 190 G |
| G | C | P | V | M | N | L | H | A |
| | | | | | | | | 200 E |
| Y | T | T | S | F | E | S | F | I |
| | | | | | | | | 210 D |
| K | V | I | W | Y | N | F | Y | K |
| | | | | | | | | 220 P |
| I | V | Y | V | G | T | D | S | A |
| | | | | | | | | 230 E |
| E | E | E | I | L | L | E | V | S |
| | | | | | | | | 240 L |
| V | F | K | I | K | E | F | A | P |
| | | | | | | | | 250 D |
| A | P | L | Y | T | G | P | A | Y | wherein G is glycine, A is alanine, V is valine, L is leucine, I is isoleucine, S is serine, T is threonine, D is aspartic acid, E is glutamic acid, N is asparagine, Q is glutamine, K is lysine, R is arginine, C is cysteine, M is methionine, F is phenylalanine, Y is tyrosine, W is tryptophan, H is histidine, and P is proline.

3. An isolated polyhedrin gene of *Spodoptera litura* nuclear polyhedrosis virus (SlNPV C-411) having the following base sequence:

```
           10           20           30           40
       GATAAAATTT   TAAAATTTTA   ATCTATAGAT   AGAAAGATAA
           50           60           70           80
       AATTTTAATC   TATAGATAAA   AGTAAAGTAT   TTAGATAAAA
           90          100          110          120
       TTTTATCTAA   AAATTTTAAT   CTAAAGATAA   AATATTGACA 130          140          150     Ⓢ ┌─→160
       TGCGATTTCT   CAATACCAAT   GAAGATCAAG   TGATGATAAG
          170          180          190          200
       GAATTTATTA   CTATCGTTCT   AGATAGTGAA   AAATCAAATA
          210          220          230          240
       TCCCATAATG   TATAGTCGCT   ACAGTGCCTA   CAATTATAGT
          250          260          270          280
       CCCCATCTGG   GCAAAACCTA   TGTATACGAT   AACAAGTATT
          290          300          310          320
       ACAAAAATTT   AGGTCACGTG   ATCAAAAATG   CTAAGCGCAA
          330          340          350          360
       ACACGATGCT   CTCGAACGCG   AGGCCGACGA   GCGCGAGCTC
          370          380          390          400
       GATCACCTAG   ACAAGTATCT   AGTCGCCGAA   GATCCGTTCA
          410          420          430          440
       TGGGTCCCGG   TAAAAATCAA   AAGTTGACTC   TGTTCAAGGA
          450          460          470          480
       GATCCGTAAC   GTGAAACCCG   ACACGATGAA   GCTGATCGTC
          490          500          510          520
       AACTGGAACG   GCAAAGAGTT   TCTCCGTGAG   ACTTGGACCC
          530          540          550          560
       GTTTCATGGA   AGACAGCTTC   CCCATCGTGA   ACGATCAAGA
          570          580          590          600
       AGTGATGGAC   GTGTTTCTAG   TGGTGAACAT   GCGTCCCACT
          610          620          630          640
       AGACCGAACC   GTTGCTTTAG   ATTTTTGGCG   CAACACGCGC
          650          660          670          680
       TCCGATGCGA   CCCCGAGTAC   GTTCCCCACG   ACGTGATCCG
          690          700          710          720
       CATCGTCGAA   CCGTCGTACG   TCGGCACCAA   CAATGAATAC
          730          740          750          760
       CGCATCAGTC   TCGCCAAGAA   AGGTGGCGGT   TGTCCCGTGA
          770          780          790          800
       TGAACCTGCA   CGCCGAATAC   ACCACTTCGT   TTGAGAGTTT
          810          820          830          840
       CATCGACAAG   GTGATATGGT   ACAACTTTTA   CAAGCCCATC
          850          860          870          880
       GTGTACGTGG   GCACCGATTC   GGCCGAAGAG   GAGGAGATCC
          890          900          910          920
       TTCTCGAAGT   GTCGCTCGTG   TTCAAGATCA   AAGAGTTTGC
          930          940          950          960
       TCCCGACGCG   CCACTCTACA   CCGGTCCCGC   GTACTAAATT
          970          980          990         1000
       TGCGAAGAGG   ACAGTCGAGC   CAGTTCGTCG   ACTCTCCGTT
```

-continued

```
    1010        1020        1030        1040
TGAGCTGTGC  AATTTTTTCG  TCGTCTTTGT  CGTCGCGACG
    1050        1060        1070        1080
CTTCTGAAGC  ATACTTTCG   CCTTTGCGAT  GTCATCGTTT
    1090        1100        1110        1120
ACGATAAAGT  ATTCGACGGC  TCGCAAAAAT  CTCTCTCTGG
    1130        1140        1150        1160
ACATTGTGTC  CGCTCGGTCG  CCGTTTGCCG  CCTCTTTGAC
    1170        1180        1190        1200
CGCGCTCGGC  TCTGCGTCTT  TAAACATAAA  CTGAACAATA
    1210        1220        1230        1240
GACATCGTCC  GTTCGACGCT  GTCAATGAGC  CGCAAAGCGT
    1250        1260        1270        1280
CATCTTTCGC  AACGATATTT  TTTACATTGT  TTAAATCTCG

1290    ↑(T) 1300     1310        1320
AAGTATATCG  GCCACGTTGC  TTTGTATAAT  TTGGCTGTTT
```

4. A vector containing a polyhedrin gene of *Spodoptera litura* nuclear polyhedrosis virus (SlNPV C-411), wherein at least part of said polyhedrin gene is replaced with a heterologous DNA sequence.

5. A vector containing a promoter of polyhedrin gene of *Spodoptera litura* nuclear polyhedrosis virus (SlNPV C-11) upstream from the 5' end of a heterologous DNA sequence and a fragment of the polyhedrin gene downstream from the 3' end of the heterologous DNA sequence.

6. A method of producing a vector, comprising:
(a) cleaving the polyhedrin gene of *Spodoptera litura* nuclear polyhedrosis virus (SlNPV C-411) to produce a DNA fragment comprising a polyhedrin promoter and sufficient flanking DNA sequences to facilitate recombination;
(b) inserting said DNA fragment into a cloning vehicle to obtain a modified cloning vehicle; and
(c) inserting at least one heterologous DNA sequence into the modified vehicle so that the heterologous DNA sequence is under the transcriptional control of the polyhedrin promoter.

7. A recombinant *Spodoptera litura* nuclear polyhedrosis (SlNPV C-411) virus wherein at least a part of the polyhedrin gene is replaced with a heterologous DNA sequence.

8. A recombinant *Spodoptera litura* nuclear polyhedrosis (SlNPV C-411) virus containing a heterologous DNA sequence which is ligated downstream of a 5'-upstream polyhedrin promoter and which is ligated upstream of a 3'-downstream DNA fragment of the polyhedrin gene.

9. A method of producing a recombinant virus, comprising:
(a) cleaving a polyhedrin gene of *Spodoptera litura* nuclear polyhedrosis virus (SlNPV C-411) to produce a DNA fragment comprising a polyhedrin promoter and sufficient flanking DNA sequence to facilitate recombination;
(b) preparing a vector by inserting the DNA fragment into a cloning vehicle to obtain a modified cloning vehicle;
(c) inserting at least one heterologous DNA sequence into the modified cloning vehicle so that the heterologous DNA sequence is under the transcriptional control of the polyhedrin promoter, to obtain a vector; and
(d) contacting the vector with the virus (SlNPV C-411) so as to effect recombination, thereby producing a mixture of recombinant and non-recombinant viruses (SlNPV C-411).

10. Cells infected with the recombinant virus described in item 7.

11. Cells infected with the recombinant virus described in item 8.

12. A method for producing a polypeptide, which comprises culturing cells infected with any of the above described recombinant viruses.

13. A method of producing a polypeptide, which comprises:
(a) preparing a recombinant *Spodoptera litura* nuclear polyhedrosis (SlNPV C-411) virus wherein the DNA contains a heterologous DNA sequence which is ligated downstream of a 5'-upstream polyhedrin promoter and which is ligated upstream of a 3'-downstream DNA fragment of the polyhedrin gene; and
(b) culturing a cell infected with the recombinant virus to produce a fused protein comprising a polypeptide sequence corresponding to the heterologous DNA sequence and at least a part of the polyhedral protein.

14. A recombinant gene, comprising a polyhedrin gene of the *Spodoptera litura* nuclear polyhedrosis virus SlNPV C-411, wherein at least part of said polyhedrin gene is replaced with a heterologous DNA sequence.

15. A recombinant gene, comprising a promoter of a polyhedrin gene of the *Spodoptera litura* nuclear polyhedrosis virus SlNPV C-411 5'-upstream from the 5' end of a heterologous DNA sequence and a fragment of said polyhedrin gene 3'-downstream from the 3' end of said heterologous DNA sequence.

16. A fusion protein, produced by a process, comprising:
culturing a cell which is infected with a recombinant virus in which a heterologous DNA sequence is ligated downstream from a 5'-upstream fragment of a polyhedrin gene of the *Spodoptera litura* nuclear polyhedrosis virus SlNPV C-411 containing a polyhedrin promoter and which is ligated upstream of a 3'-downstream fragment of said polyhedrin gene, for a time sufficient to accumulate said fusion protein.

17. A fusion protein, comprising a polypeptide which is fused to at least part of the polyhedrin peptide of the *Spodoptera litura* nuclear polyhedrosis virus SlNPV C-411.

BRIEF DESCRIPTION OF THE DRAWINGS

FIG. 1 shows parts of the polyhedrin genes of AcMNPV, BmNPV, and viruses of *Orygia pseudot-* sugata (hereinafter referred to simply as OpMNPV and OpSNPV) i.e. the base sequences of probes 1 and 2.

Figure 2A:
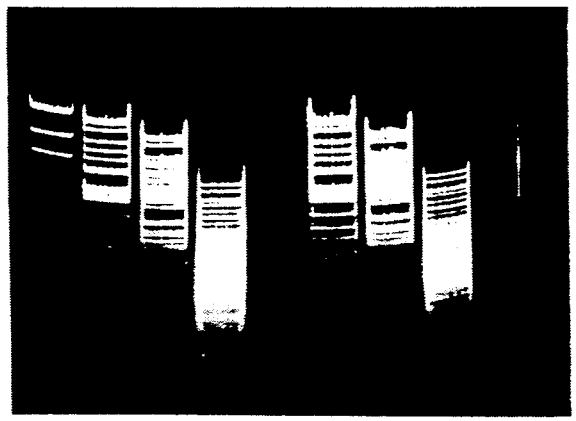
Figure 2B:
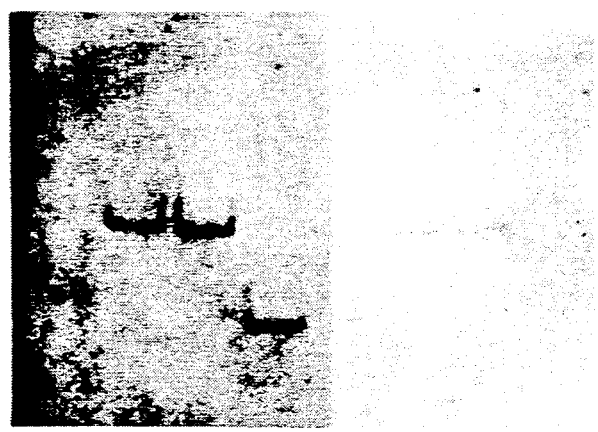

FIG. 2-a is a photograph showing the restriction enzyme cleavage pattern of the polyhedrin gene of SlNPV C-411, and FIG. 2-b is a photograph showing the hybridization pattern of the polyhedrin gene by probe 1 or 2.

Figure 3:
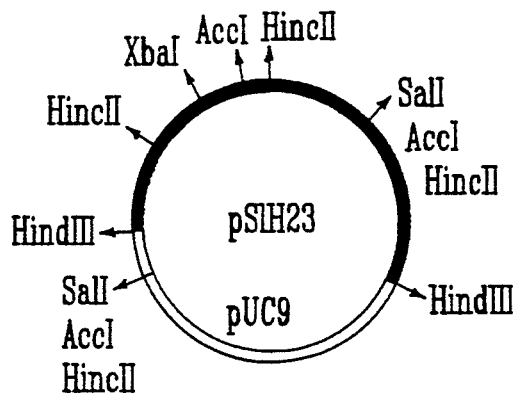

FIG. 3 shows the restriction enzyme cleavage map of the polyhedrin gene of SlNPV C-411.

FIG. 4 shows the base sequence and the amino acid sequence of the polyhedrin gene of SlNPV C 411.

FIG. 5 shows the 5'-upstream base sequences of the polyhedrin genes of AcMNPV, BmNPV, OpMNPV and OpSNPV.

Figure 6A:
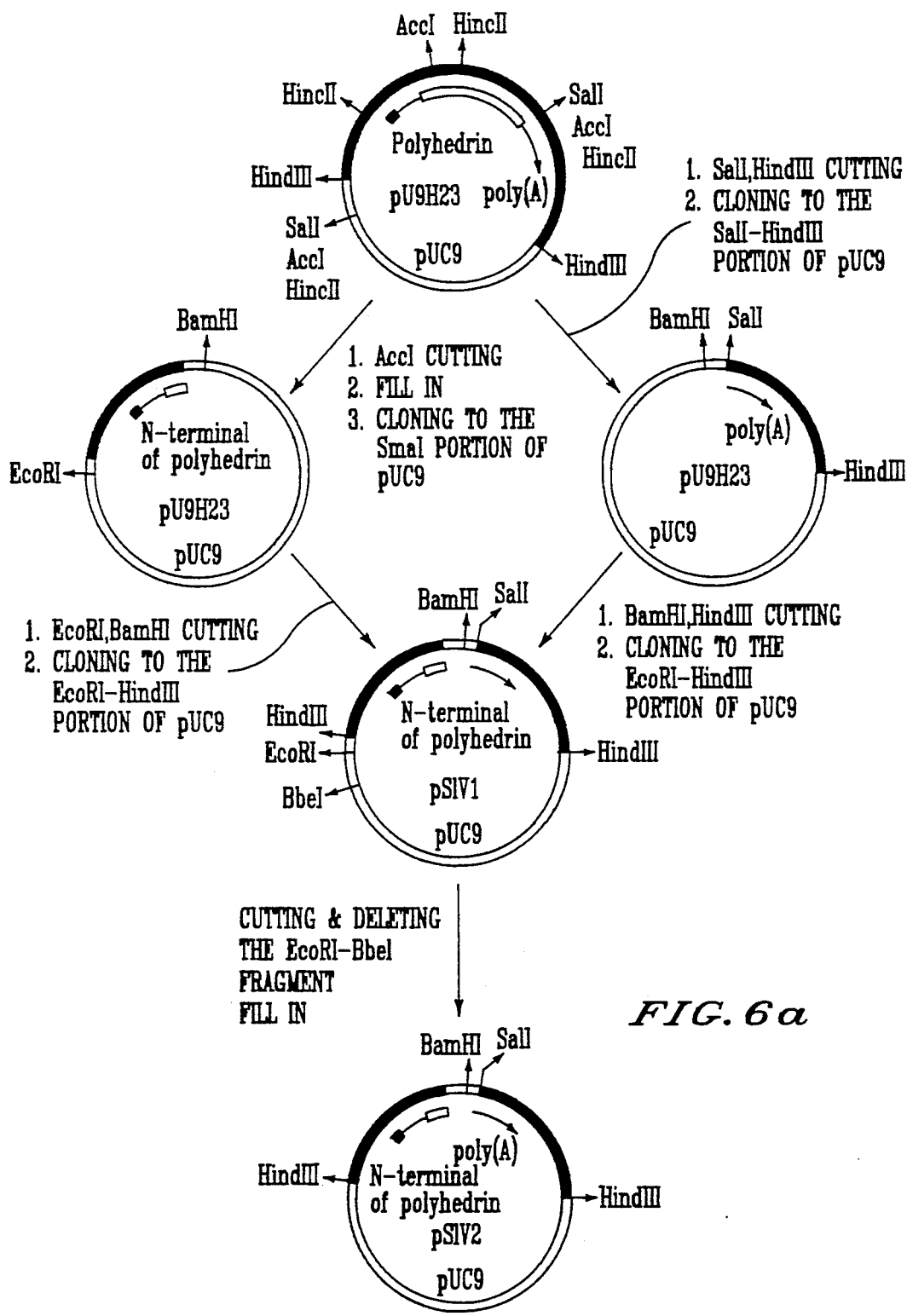
Figure 6B:
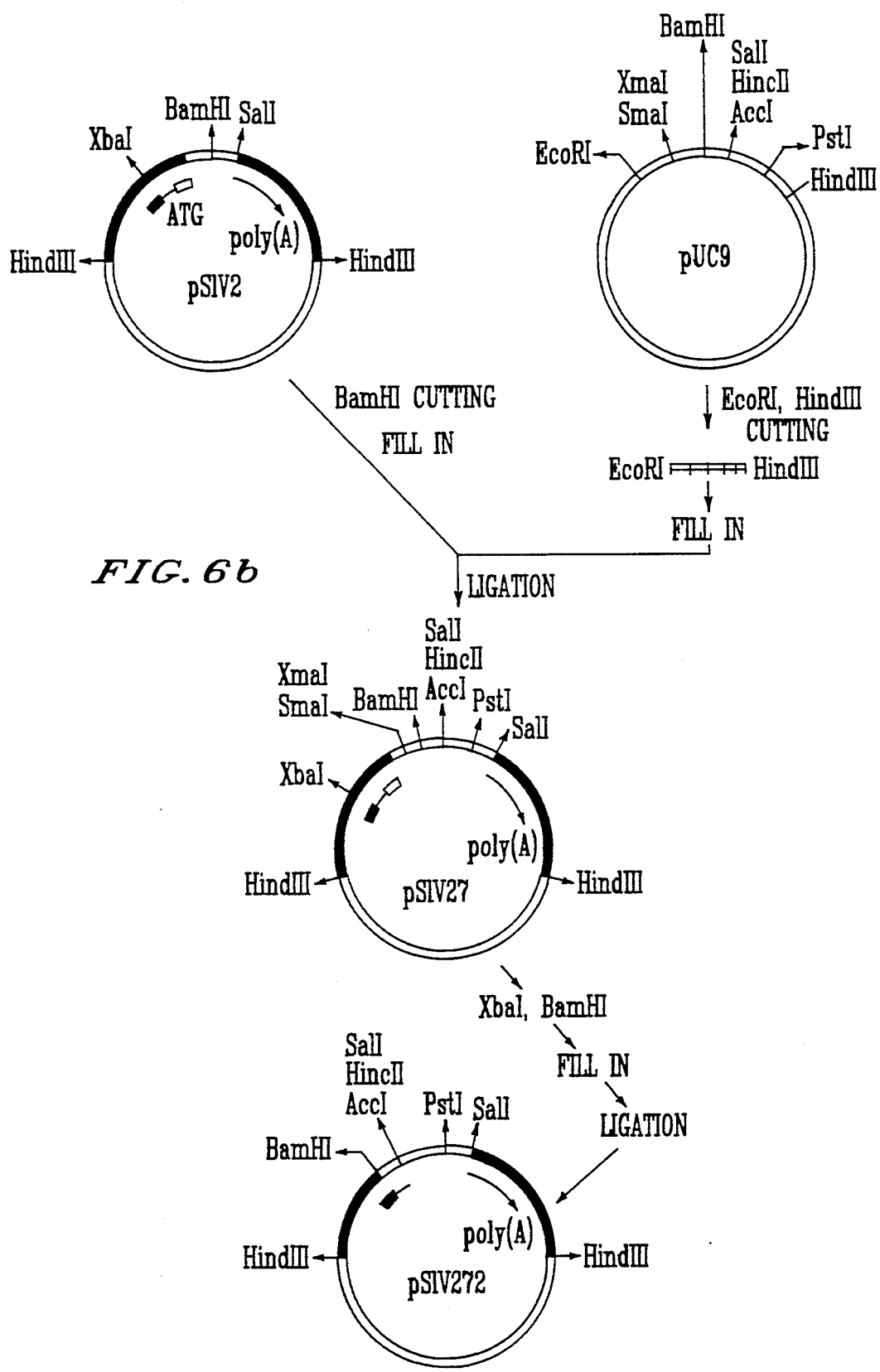

FIG. 6-a illustrates the construction of a vector I, and FIG. 6-b illustrates the construction of a vector II.

Figure 7:
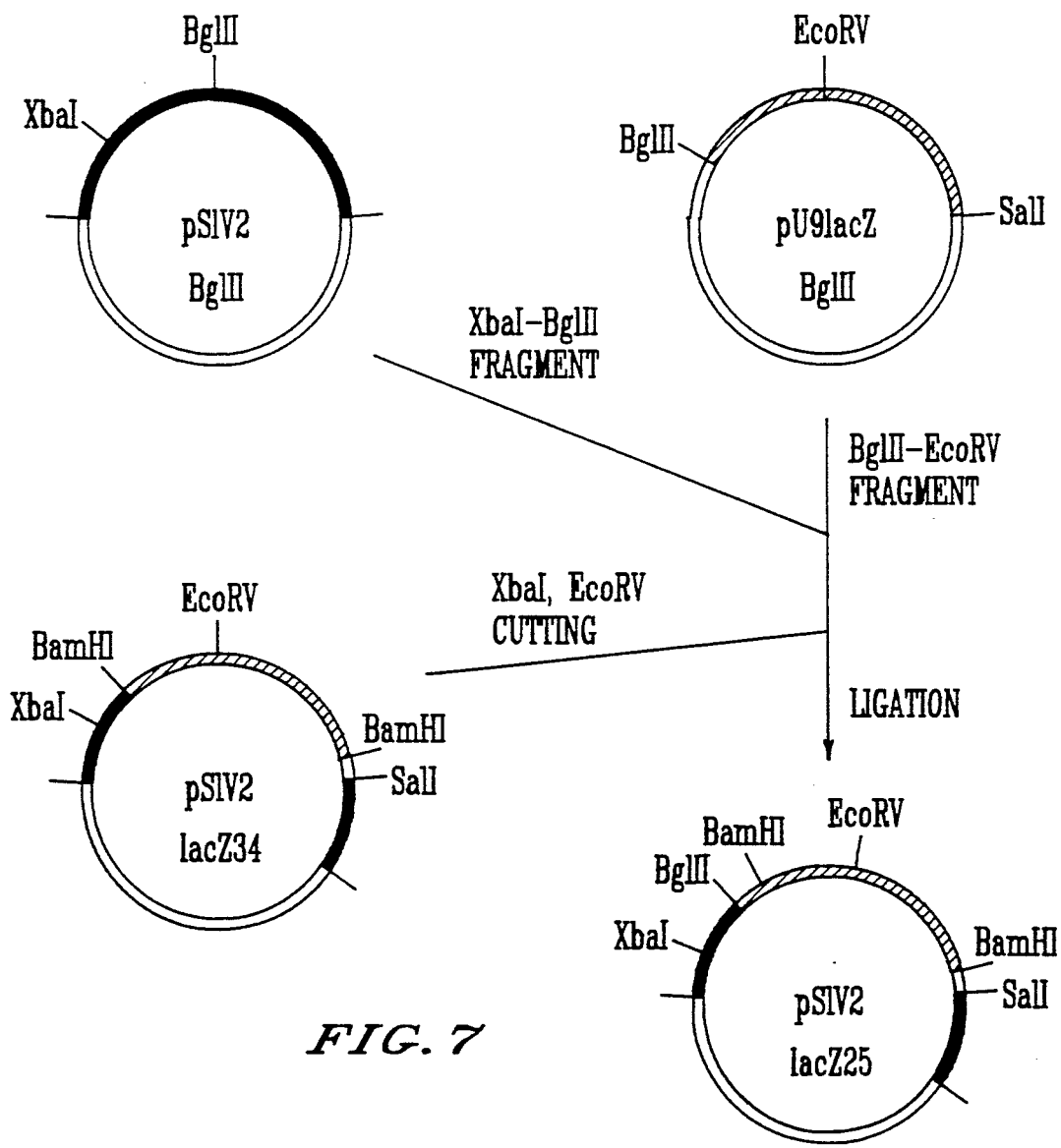

FIG. 7 illustrates the cloning of $\beta$-galactosidase.

Figure 8A:
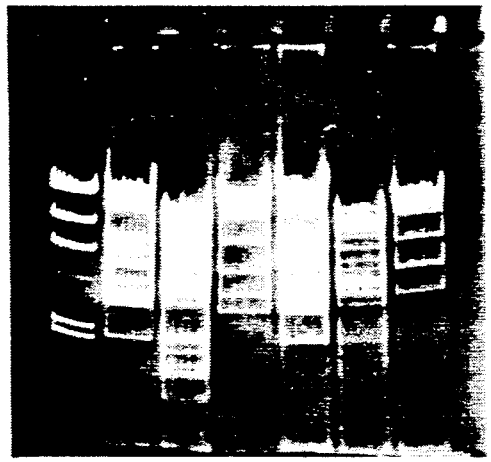
Figure 8B:

FIG. 8-a is a photograph showing the restriction enzyme cleavage patterns of the genes of SlNPV C-411 and SlNPV $\beta$-gal2, and FIG. 8-b is a photograph showing the hybridization pattern of the genes.

Figure 9:
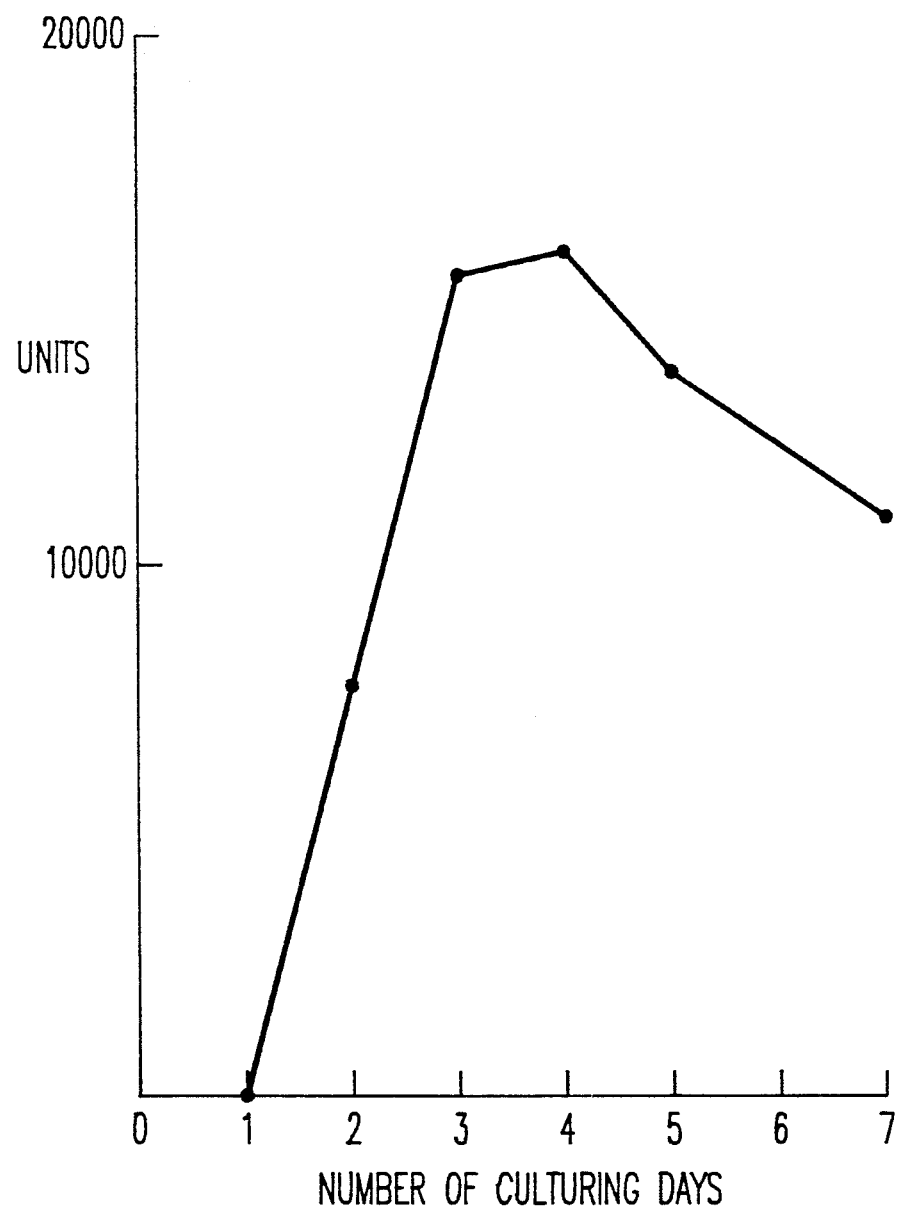

FIG. 9 is a graph showing the production of $\beta$-galactosidase by SlNPV $\beta$-gal2.

Figure 10A:
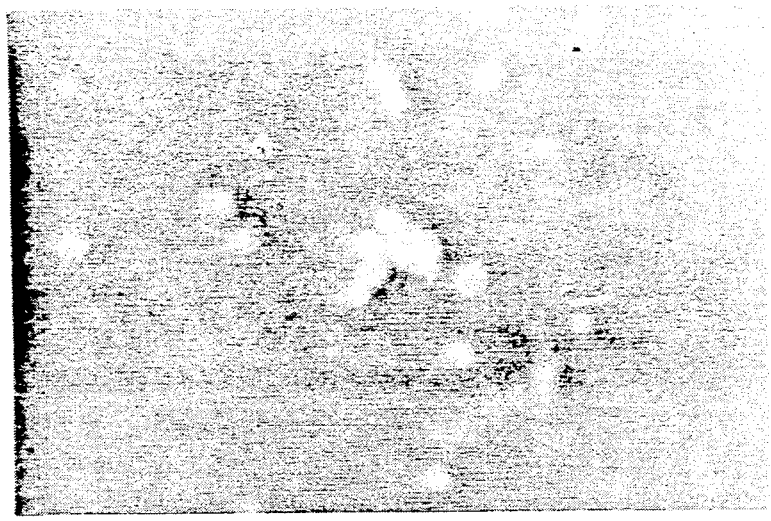
Figure 10B:
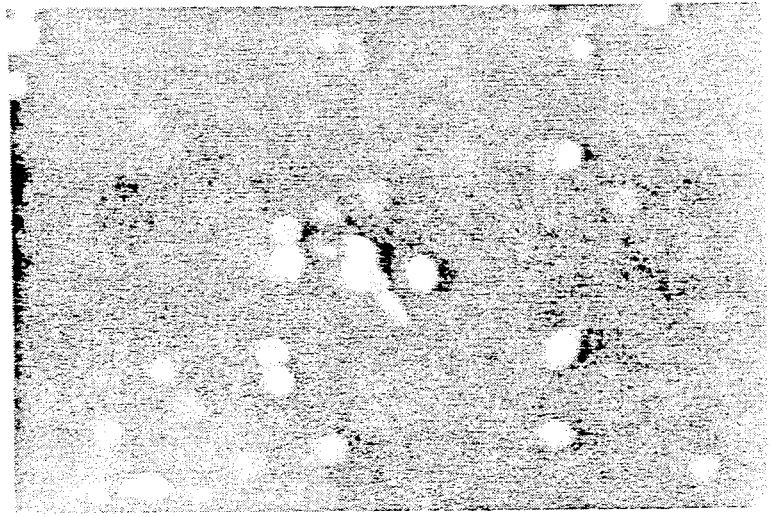

FIG. 10-a is a photograph showing cells infected with SlNPV C-411, and

FIG. 10-b is a photograph showing cells infected with SlNPV $\beta$-gal2.

Figure 11:
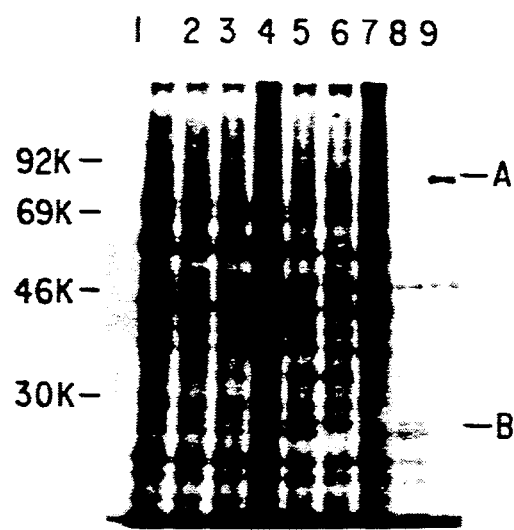

FIG. 11 is a photograph showing the expression of $\beta$-galactosidase by pulse labeling.

DETAILED DESCRIPTION OF THE PREFERRED EMBODIMENTS

The present inventors have studied the polyhedrin gene of *Spodoptera litura* nuclear polyhedrosis virus (SlNPV). In the present invention, operational techniques commonly employed in genetic engineering, such as the synthesis (chemical synthesis, or cleavage by restriction enzymes), separation and detection of DNA fragments, the analysis of DNA sequence and the treatment of e.g. *Escherichia coli* (such as transformation, culturing and preparation of a plasmid), can be applied (see: T. MANIATIS et al (1982): Molecular Cloning, Cold Spring Harbor Laboratory). The polyhedra of SlNPV are purified and dissolved by an alkali, and occluded virus (OV) of SlNPV thereby released infects and propagates in the CLS-79 strain (obtained from the Agricultural Department of Kyushu University) of *Spodoptera littoralis* cells originated in Egypt. NOV of SlNPV refers to the virus formed by budding from cells and passing through the plasma membrane. Plaques are formed by a plaque-forming method by means of a sea plaque agarose. A similar operation is repeated three times to obtain a monoclonal virus, which is designated as SlNPV C-411. DNA of SlNPV C-411 may be obtained from NOV propagated in cultured cells. However, the following method is simple and better suited to obtain it in a larger amount (see: Kobayashi, M. (1984): Appl. Ent. Zool., 19(3), 280-287 and S. T. TZIA et al (1979): Virology, 99, 399-409). This SlNPV C-411 may be propagated by means of the abovementioned CLS-79 strain and then injected into the abdomen of third instar larvae of *Spodoptera litura*. About seven days later, the larvae will die, and the hemolymph of the larvae containing polyhedra of the virus are collected. This hemolymph is subjected to filtration and centrifugation to purify the polyhedra. Then, the polyhedra are dissolved with an alkali to release the virus. The virus is purified by sucrose density gradient centrifugation, ultra centrifugation or the like. This virus is treated with proteinase K to decompose the protein and then subjected to phenol treatment to obtain DNA of the cloned virus SlNPV C-411 having a length of about 130 kilobase pairs.

This DNA is cleaved by means of various restriction enzymes, then electrophoresed in an agarose gel having a concentration of from 0.5 to 1.5%, preferably 0.7%, then transferred to a nitrocellulose filter paper and subjected to Southern hybridization. As probes, two strands of DNA are chemically synthesized based on a polyhedrin gene of a well conserved polyhedrosis virus heretofore reported, such as a polyhedrin gene of AcMNPV, BmNPV or *Orygia pseudotsugata* (OpSNPV or OpMNPV), and their terminal ends are labeled with $^{32}$p for use. As a result, a positive fragment of about 3 kilobase pairs is obtained, and the majority of the base sequence thereof is determined by a dideoxy chain termination method. That fragment has two portions which respectively correspond to the base sequences of the synthesized DNAs used as the probes. The base sequence of 747 base pairs containing the two portions is capable of encoding a protein having 249 residues of amino acids. Such a protein has a size larger than the polyhedrin proteins of known nuclear polyhedrosis viruses including the abovementioned AcMNP since it is longer by 3 or 4 residues of amino acids at its N terminal portion than the known polyhedrin proteins composed of 245 or 246 residues of amino acids. Therefore, this protein is definitely different from the known proteins. Further, the amino acid sequences of two fragments among the peptide fragments obtained by cleaving the purified polyhedrin protein with cyanogen bromide, were examined by an Edman degradation method and were found to completely agree with the amino acid sequences assumed from the DNAs as determined above.

From these facts, these DNA fragments are considered to contain the polyhedrin gene of SlNPV C-411. With known polyhedrosis viruses AcMNPV, BmNPV, the left hand sides of their initiation codons (ATG) i.e. the 5'-upstream regions of 71 base pairs completely agree with each other, whereas the polyhedrin gene of SlNPV C-411 of the present invention is definitely different in this respect from the genes of the known viruses and has a base sequence which is different also from the base sequences of known OpSNPV and OpMNPV. Thus, the polyhedrin gene of SlNPV C-411 of the present invention is different from the polyhedrin genes of known nuclear polyhedrosis viruses and novel.

The polyhedrin protein is not required for the propagation of the nuclear polyhedrosis virus in the culturing cells. Therefore, it is possible to prepare a recombinant virus by replacing the gene coding for this protein with a structural gene coding for another useful substance, then infect cells with the recombinant virus and cultivate the infected cells for the production of the useful substance. Namely, the portion of the polyhedrin gene coding for the polyhedrin protein of SlNPV C-411 is at the center of a positive fragment of about 3 kilobase pairs. About 1.1 kilobase pairs 5'-upstream from the initiation codon is the sequence containing a polyhedrin promoter, and about 1.2 kilobase pairs 3'-downstream from the termination codon is the portion containing a poly A additional site. By inserting a gene coding for a useful substance in substitution for DNA of the center portion coding for the polyhedrin protein, it is possible to produce the useful substance on the basis of a different gene under the control of the polyhedrin promoter.

Now, an embodiment for constructing a vector using this polyhedrin protein gene of SlNPV C-411 will be described. The polyhedrin protein gene of SlNPV C-411 is inserted in a vector or vehicle such as an *Escherichia coli* vector pBR322, pUC-type vector, in accordance with the conventional method. The polyhedrin gene of SlNPV C-411 has a restriction enzyme AccI cutting site around about 20 amino acids from the N terminal residue and a restriction enzyme SalI cutting site at the 3'-side in the vicinity of the translation terminal signal. The portion between AccI and SalI is removed and a linker is inserted. Then, another gene is ligated there to produce a fused protein. Further, using a XbaI site located upstream of the initiation codon, the portion between the XbaI site and the AccI site is removed, and a polylinker is inserted there, whereby it is possible that the gene coding for a useful substance is translated from the initiation codon thereof, and it is also possible to produce a protein on the basis of only the gene coding for the useful substance. Namely, of the DNA fragment of about 3 kilobase pairs containing DNA coding for the polyhedrin of SlNPV C-411, the Hind III-AccI fragment of about 1.1 kilobase pairs containing the polyhedrin promoter and the SalI-Hind III fragment of about 1.2 kilobase pairs containing the poly A additional site are inserted in the commercially available plasmid pUC9 with a Bam HI linker sandwiched therebetween, to obtain a vector which is capable of producing a fused protein. The size of this vector is about 5 kilobase pairs, and a gene coding for a useful substance is inserted to match the reading frame to the Bam HI linker portion.

The vector of the present invention is small as compared with known vectors of AcNPV and BmNPV which have a length of about 10 kilobase pairs. Therefore, for the cloning of the gene coding for a useful substance, the efficiency of transformation with *Escherichia coli* is excellent, and a useful substance on the basis of a larger gene can readily be cloned.

The vector of the present invention can be embedded directly in the chromosome of cells. Further, by introducing DNA of this vector and wild type viral DNA together into insect cells of *S. littoralis* CLS-79-C7 strain (deposited at the Fermentation Research Institute, Agency of Industrial Science and Technology, Ministry of International Trade and Industry of Japan: accession number FERM BP-2723), it is possible to prepare a recombinant virus by homologous recombination. Such a recombinant virus can be selected by plaque hybridization or by means of a suitable marker. The promoter of the polyhedrin gene is powerful and controlled to function at a later stage of infection with the virus, whereby the polyhedrin protein of wild type virus SlNPV C-411 is produced in a large amount at a later stage of infection. For example, by infecting cells of *S. littoralis* CLS-79-C7 strain with the selected recombinant virus and culturing the infected cells at 27° C., it is possible to obtain a large amount of a protein transcribed and translated by the polyhedrin promoter at a later stage of the propagation of the virus. The S. littoralis CLS-79-C7 strain is a strain cloned from the parent *S. littoralis* CLS-79 strain, which is suitable for the suspension culture and the propagation of the virus, whereby it is possible to produce a protein in a large amount by culturing the cells and propagating the virus. Cells to be used in the present invention include the *S. littoralis* CLS-79-C7 strain, *Spodoptera fruqiperda* sf-9 strain and the like.

Thus, in the present invention the heterologous DNA sequences correspond to genes for producing useful substances which include, for example, enzymes, interferon ($\alpha,\beta,\gamma$) interleukin (1-6), insulin, human growth hormones, various mammalian growth hormones, somatomedins, various peptides, proteins or glycoproteins such as lymphokines, gp160 (gp120, gp41) protein of AIDS virus, HBs protein of B-type hepatitis virus; proteins of various viruses and receptor proteins of various cells. Of course, it will be recognized by those skilled in the art that any heterologous sequences of DNA may be inserted in the present vectors and recombinant viruses. Any size of genes coding for useful substances to be used in the present invention can not be defined generally, if these genes can be cloned in the vector. Among these genes, genes having no more than 5 kilobase pairs are preferred, and genes having a range of from 500 base pairs to 5 kilobase pairs are more preferred. By means of the vector of the present invention, it is possible to express these genes coding for useful substances. Further, the vector of the present invention is useful also for genes of many natural substances which may be isolated in the future, particularly for those requiring the modification of the proteins.

Now, the present invention will be described in further detail with reference to specific Examples. However, it should be understood that the present invention is by no means limited by such specific Examples.

EXAMPLE 1

Figure 1:
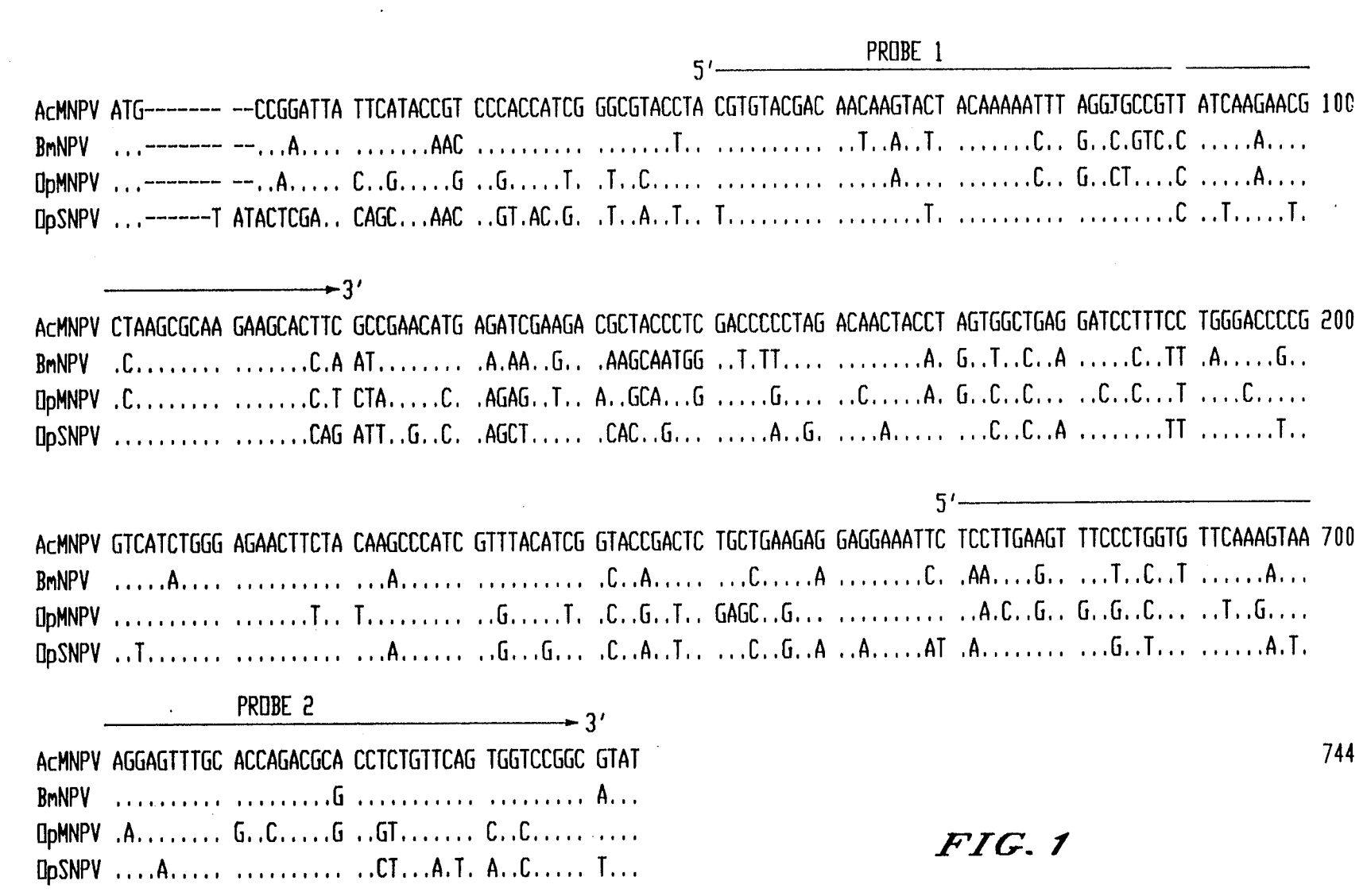

Detection of the polyhedrin gene from DNA of SlNPV C-411 by Southern hybridization About 0.1 µg of DNA obtained from the polyhedra of SlNPV C-411 was cleaved with restriction enzymes Hind III (manufactured by Takara Shuzo K.K., all the restriction enzymes hereinafter mentioned were manufactured by Takara Shuzo K.K.) and Bam HI, Hind III and Eco RI, or Hind III and Hinc II. Then, the fragments were subjected to electrophoresis using a 0.7% agarose gel, then transferred to a nitrocellulose filter paper and subjected to hybridization at 42° C. As probes 1 and 2, two DNA fragments of 70 bases were chemically synthesized by means of a DNA synthesizer manufactured by Applied Biosystems Co., on the basis of the base sequence (FIG. 1) at two portions of the polyhedrin gene of *Autoqrapha californica* nuclear polyhedrosis virus (AcMNPV) which was well conserved as a polyhedrin gene of other nuclear polyhedrosis virus, and the terminal ends of the DNA fragments (about 0.1 µg) were labeled with $\gamma\text{-}^{32}\text{p-dATP}$ for use as probes.

As a result, when DNA was cleaved with Hind III and BamHI, or Hind III and Eco RI, a positive fragment of about 3 kilobase pairs was observed, as shown in FIG. 2. This positive fragment was found to be a fragment cut only by Hind III, as a result of the cloning operation.

Therefore, it was cloned to the Hind III site of pUC9 (obtained from the Medical Department of Kyushu University) to obtain pSlH23. DNA (about 1 µg) of the Hind III fragment of this pSlH23 was further cleaved with restriction enzymes, followed by Southern hybridization in the same manner as described above, whereby one probe hybridized with the Hinc II fragment of 0.7 kilobase, and the other probe hybridized with the Hinc II fragment of 0.6 kilobase. As a result, the restriction enzyme cleavage map (pSlH23) as shown in FIG. 3 was determined. This pSlH23 was introduced into *Escherichia coli* JM 83 strain (obtained from the Medical Department of Kyushu University) and deposited as *Escherichia coli* JM 83: pSlH23 at the Fermentation Research Institute, Agency of Industrial Science and Technology, Ministry of International Trade and Industry of Japan. The accession number is FERM BP-2721.

EXAMPLE 2

Determination of the base sequence of DNA

About 1 μg of the positive DNA fragment cloned to the Hind III site of pUC9, was further fragmented and cloned with reference to the restriction enzyme cleavage map of FIG. 3, and the major portion of the base sequence was determined by a dideoxy chain termination method. As a result of the computer analysis, DNA of 747 base pairs capable of encoding a protein composed of 249 amino acids was found to exist at about the center of the fragment of about 3 kilobase pairs, as shown in FIG. 4. The amino acid sequence assumed from the DNA by the computer analysis showed a homology of at least 80% with respect to the portion conserved as the polyhedrin gene heretofore reported. However, as compared with the polyhedrins of nuclear polyhedrosis viruses of *Autoqrapha californica* (Ac), *Bompyx mori* (Bm) and *Origia pseudotsugata* (Op) i.e. AcMNPV (245 residues of amino acid), BmNPV (245 residues thereof), OpMNPV (245 residues thereof) and OpSNPV (246 residues thereof), this DNA has a N-terminal longer by 3 or 4 amino acid residues. On the other hand, about 500 μg of the purified polyhedrin protein of SlNPV C-411 was cleaved by cyanogen bromide into fragments, which were purified by reverse phase high performance chromatography. With respect to two fragments among them, the sequences of ten amino acids from the N-terminal ends were examined by an Edman degradation method, whereby the amino acid sequences of these fragments (in FIG. 4, the amino acid sequences from the 2nd to the 11th and from the.66th to the 75th) and the amino acid sequences assumed from the base sequences of DNA agreed completely. This indicates that these DNA fragments contain a gene coding for the polyhedrin protein of SlNPV C-411.

Further, the present polyhedrin protein is a novel protein which has not been disclosed in the literature.

Of this DNA fragment, the upstream portion from the initiation codon (ATG) contains many A and T as in the cases of polyhedrins of other nuclear polyhedrosis viruses. AcMNPV and BmNPV have the same 71 bases at the 5'-upstream portion from the respective initiation codons, whereas the corresponding sequence of SlNPV C-411 is apparently different from the sequence of AcMNPV or BmNPV. Further, the sequence of SlNPV C-411 is apparently different from those of OpMNPV and OpSNPV. The transcription initiation site of this SlNPV C-411 is considered to be the site indicated by an arrow in FIG. 4, as a result of SI mapping.

EXAMPLE 3

Preparation of a vector

The vector was prepared using the 5'-upstream region containing the initiation codon of the polyhedrin gene of SlNPV C-411 and the 3'-downstream region from the termination codon. The vector I has a Hind III-AccI fragment as the 5'-upstream region and a SalI-Hind III fragment as the 3'-downstream region, with a Bam HI linker inserted therebetween as a cloning site. To this site, a gene coding for a useful substance is inserted to match the reading frame, whereby a protein having 19 amino acids of the N-terminal end of the polyhedrin protein of SlNPV C-411 is assumed to be produced (FIG. 6-*a*). The vector II has a Hind III-XbaI fragment as the 5'-upstream region and a SalI-Hind III fragment as the 3'-downstream region, with a polylinker inserted therebetween, so that the gene coding for a useful substance having the initiation codon (ATG) can be expressed as a single protein (FIG. 6-*b*). Each of these vectors has a length of about 5 kilobase pairs.

EXAMPLE 4

Cloning of a β-galactosidase gene

Insertion of a β-galactosidase gene into the vector I

As shown in FIG. 7, to match the reading frames of the N-terminal portions of the β-galactosidase gene and the polyhedrin gene, the Bam HI site of the vector I was cut and filled in with nucleotides, and a Bgl II linker was inserted. As the lacZ gene, the corresponding portion was taken out from a commercially available plasmid pMC1871 (manufactured by Phamacia Co.). A total of six amino acids other than those of the polyhedrin and the β-galactosidase, were added including those of the linker, etc. (pSlV2 lacZ25 in FIG. 7). This pSlV2 lacZ25 was introduced into *Escherichia coli* HB101 strain . (obtained from the Medical Department of Kyushu University) and deposited as *Escherichia coli* HB101: pSlV2 lacZ25 at the Fermentation Research Institute, Agency of Industrial Science and Technology, Ministry of International Trade and Industry of Japan. The accession number is FERM BP-2722.

2) Preparation of a recombinant virus bV mixing a vector DNA with wild-type virus SlNPV C-411 DNA in insect cells of *S. littoralis* CLS-79-C7 strain Into a Petri dish having a diameter of 6 cm, $2.5 \times 10^5$ cells/ml of *S. littoralis* CLS-79-C7 strain was introduced in an amount of 4.5 ml and left to stand at room temperature for one hour. Then, an aggregate of DNA prepared by adding 50 μl of 2.5 M $CaCl_2$ to 1 ml of HEBS (0.137 M NaCl, 5 mM KCl, 0.7 mM $Na_2HPO_4.2H_2O$, 5.5 mM glucose, 0.021 M Hapes) of pH 7.0 containing 0.1 μg of SlNPV C-411 DNA and 10 μg of pSlV 2 lacZ25 and leaving the mixture at room temperature for 20 minutes, was dropwise added to the culture medium. The culture was left to stand at 27° C. for 4 hours, and then the culture medium was removed. Then, about 0.5 ml of a 15% glycerol solution in HEBS, was added, and the mixture was left to stand for 3 minutes. Then, the glycerol solution was removed, and the residue was washed twice with 5 ml of IPL-41 culture medium (Goodwin, 1977) (Table 1) containing 10% of fetal calf serum (FCS). Then, 4.5 ml of the same culture medium was added thereto. The mixture was cultured at 27° C. for 4 days. Then, the supernatant was diluted and cultured at 27° C. for 6 days to form plaques. Then, 2 ml of a 0.75% agarose containing X-gal (5-bromo-4-chloro-3-indolyl-β-D-galactoside) and IPL-41 (10FCS) culture medium, was overlaid on the Petri dish having the plaques formed, followed by culturing at 37° C. for 4 hours. Then, a blue plaque was taken, and the plaque-formation was repeated three times to purify the virus.

The obtained virus was used in the subsequent experiments as recombinant virus SlNPV β-gal2.

TABLE 1

| IPL-41 culture medium (pH 6.4) Components | mg/l |
|---|---|
| NaH₂PO4 H₂O | 1160.0 |
| NaHCO₃ | 350.0 |
| KCl | 1200.0 |
| CaCl₂ | 500.0 |
| MgSO₄ 7H₂O | 1880.0 |
| (NH4)₆Mo₇O₂₄ 4H₂O | 0.04 |
| CoCl₂ 6H₂O | 0.05 |
| CuCl₂ 2H₂O | 0.20 |
| MnCl₂ 4H₂O | 0.02 |
| ZnCl₂ | 0.04 |
| FeSO₄ 7H₂O | 0.55 |
| L-arginine hydrochloride | 800.0 |
| L-asparatic acid | 1300.0 |
| L-asparagine | 1300.0 |
| β-alanine | 300.0 |
| L-cystine | 100.0 |
| L-glutamic acid | 1500.0 |
| L-glutamine | 1000.0 |
| L-glycine | 200.0 |
| L-histidine | 200.0 |
| L-hydroxyproline | 800.0 |
| L-isoleucine | 750.0 |
| L-leucine | 250.0 |
| L-lysine hydrochloride | 700.0 |
| L-methionine | 1000.0 |
| L-proline | 500.0 |
| L-phenylalanine | 1000.0 |
| DL-serin | 400.0 |
| L-tyrosine | 250.0 |
| L-tryptophan | 100.0 |
| L-threonine | 200.0 |
| L-valine | 500.0 |
| sucrose | 16500.0 |
| maltose | 1000.0 |
| glucose | 2500.0 |
| malic acid | 53.6 |
| α-ketoglutaric acid | 29.6 |
| succinic acid | 4.8 |
| fumaric acid | 4.4 |
| thiamine hydrochloride | 0.080 |
| riboflavin | 0.080 |
| calcium pantothenate | 0.008 |
| pyridoxy hydrochloride | 0.400 |
| p-aminobenzoic acid | 0.320 |
| folic acid | 0.080 |
| niacin | 0.160 |
| isoinositol | 0.400 |
| biotin | 0.160 |
| cyanocobalamin | 0.240 |
| choline chloride | 20.000 |
| triptose broth (manufactured by Difco Co.) | 2600.0 |

3) Ascertaining the insertion of the β-galactosidase gene into the SlNPV β-gal2DNA Into a spinner flask having a capacity of 1l, *S. littoralis* CLS-79-C7 strain was introduced in an amount corresponding to $5 \times 10^7$ cells/500 ml (IPL-41 culture medium, 10% FCS), and the virus of SlNPV β-gal2 was infected at MOI 1 (multiplicity of infection degree 1) and cultured at 27° C. for 5 days. The virus was purified by conducting the precipitation by means of 10% polyethylene glycol (PEG precipitation), sucrose density gradient centrifugation and ultra centrifugation, followed by proteinase treatment and phenol treatment to obtain about 10 μg of SlNPV -β-gal2 DNA. About 0.1 μg of this DNA was cleaved by Bam HI, Eco RI, Hind III, then electrophoresed in a 0.7% agarose gel (FIG. 8-a), transferred to a nitrocellulose filter paper and then subjected to Southern hybridization using the β-galactosidase gene DNA (about 0.1 μg) as a probe. The β-galactosidase gene used as the probe was labeled with α-³²p-dCTP using a multi primer kit (manufactured by Amersham Co.). As a result, it was found possible to introduce other genes into SlNPV C-411 in substitution for the polyhedrin DNA of SlNPV C-411 (FIG. 8-b) by using a vector prepared from the forward and rear portions of the polyhedrin gene of SlNPV C-411 and to prepare a recombinant virus.

EXAMPLE 5

Expression of β-galactosidase

1) Measurement of the activities

To $5 \times 10^6$ cells of S. littoralis CLS-79-C7 strain cultured in a spinner flask, SlNPV C-411 or SlNPV β-gal2 was infected at MOI 25. The virus was adsorbed on the cells at 27° C. for 2 hours, then washed twice with IPL-41 culture medium (0% FCS) and then cultured in a spinner flask having a capacity of 100 ml containing 50 ml of IPL-41 culture medium (10% FCS). At every predetermined time interval, 1 ml of the culture medium was sampled, and β-galactosidase activities were examined by means of ONPG (O-nitrophenyl-β-D-galactopyranoside). The activities were the total activities including the culture medium and the cells, and the number of units was calculated in accordance with the following equation.

$$\text{Units} = \frac{1000 \times O.D._{420} - 1.75 \times O.D._{550}}{t \times V \times O.D._{600}}$$

t: reaction time (minutes)
V: amount (ml) of the culture broth used for the determined of the units.
O.D.: absorbance (optical density)

As a result, no β-galactosidase activities were observed in the case where only cells were used as a control, and in the case where the cells were infected by the SlNPV C-411. Whereas, with the cells infected by SlNPV β-gal2, activities were observed with a peak of 16,000 units on the fourth day (FIG. 9). The activities were compared between the inside of the cells and the outside of the cells (in the culture medium). The major activities were observed in the cells, and the activities outside of the cells were observed on the third and subsequent days as the cells underwent lysis. Therefore, it is believed that β-galactosidase is accumulated in the cells without being discharged from the cells.

2) Distribution of β-galactosidase in the cells

Cells put on and cultured on a cover glass were infected with SlNPV C-411 or SlNPV β-gal2 at MOI 50, then cultured at 27° C. for 2 days, treated with formaldehyde and Triton X-100, then subjected to blocking with bovine serum albumin, treated with a primary antibody (β-galactosidase antibody), further treated with a secondary antibody labeled with fluorescein isothiocyanate (FITC), and observed by a fluorescence microscope (FIG. 10-a). As a result, the wild type virus SlNPV C-411 was not stained at all, whereas the recombinant virus SlNPV β-gal2 was stained with the nucleus at the center, thus indicating a possible transfer to the nucleus (FIG. 10-b).

3) Labeling of the protein with ³³⁵S-methionine

The protein synthesized during the propagation of the virus, was labeled with ³⁵S-methionine, and the results were examined by electrophoresis by means of SDS-polyacrylamide, followed by treatment with an amplifier and radiographing on an X-ray film.

1×10⁵ Cells of S. littoralis CLS-79-C7 strain put in the wells of a plate having four wells and cultured at 27° C. for 2 hours were infected with the virus at MOI 50. After a predetermined time, the virus solution was removed, and the cells were washed once with 1 ml of methionine free IPL-41 culture medium (10% FCS). Then, 0.25 ml of a methionine free IPL-41 culture medium (10% FCS) containing 75 μCi (2775 kBq)/ml of ³⁵S-methionine was added thereto, followed by culturing for 12 or 24 hours Then, the culture medium was removed, and 100 μl of sample buffer was added to dissolve the cells, and the sample was frozen until it was used for analysis. (Sample buffer: 62.5 mM Tris-HCl (pH 6.8), 1% SDS, 0.005% bromophenol blue, 10% glycerol, 10% 2-mercaptoethanol).

As shown in FIG. 11, a polyhedrin band (about 32 kilodaltons) was observed with the cells infected with the wild-type virus, for the first time when labeled for 24 hours from 12 to 36 hours. In parallel therewith, the β-galactosidase band (about 116 kilodaltons) was observed with the cells infected with SlNPV β-gal2 virus. This indicates that the SlNPV β-gal2 virus apparently expresses β-galactosidase instead of the polyhedrin of SlNPV C-411.

According to the present invention, a gene coding for a useful substance of about no more than 5 kilobase pairs can relatively simply be cloned in a vector. Further, the gene can relatively easily be substituted for a portion of the polyhedrin gene of SlNPV C-411 to obtain a recombinant virus. Furthermore, by propagating this recombinant virus in insect cells, it is possible to produce a useful peptide, protein or glycoprotein.

Obviously, numerous modifications and variations of the present invention are possible in light of the above teachings. It is therefore to be understood that within the scope of the appended claims, the invention may be practiced otherwise than as specifically described herein.

What is claimed is:

1. An isolated polyhedrin gene of *Spodoptera litura* nuclear polyhedrosis virus having the restriction enzyme cleavage map and insert size shown in FIG. 3.

2. An isolated polyhedrin gene of *Spodoptera litura* nuclear polyhedrosis virus having a DNA sequence coding for the following amino acid sequence:

| | | | | | | | | |
|---|---|---|---|---|---|---|---|---|
| M | Y | S | R | Y | S | A | Y | N | Y |
| | | | | | | | | | 20 |
| S | P | H | L | G | K | T | Y | V | Y |
| | | | | | | | | | 30 |
| D | N | K | Y | Y | K | N | L | G | H |
| | | | | | | | | | 40 |
| V | I | K | N | A | K | R | K | H | D |
| | | | | | | | | | 50 |
| A | L | E | R | E | A | D | E | R | E |
| | | | | | | | | | 60 |
| L | D | H | L | D | K | Y | L | V | A |
| | | | | | | | | | 70 |
| E | D | P | F | M | G | P | G | K | N |
| | | | | | | | | | 80 |
| Q | K | L | T | L | F | K | E | I | R |
| | | | | | | | | | 90 |
| N | V | K | P | D | T | M | K | L | I |
| | | | | | | | | | 100 |
| V | N | W | N | G | K | E | F | L | R |
| | | | | | | | | | 110 |
| E | T | W | T | R | F | M | E | D | S |
| | | | | | | | | | 120 |
| E | P | I | V | N | D | Q | E | V | M |
| | | | | | | | | | 130 |
| D | V | F | L | V | V | N | M | R | P |
| | | | | | | | | | 140 |
| T | R | P | N | R | C | F | R | F | L |
| | | | | | | | | | 150 |
| A | Q | H | A | L | R | C | D | P | E |
| | | | | | | | | | 160 |
| Y | V | P | H | D | V | I | R | I | V |
| | | | | | | | | | 170 |
| E | P | S | Y | V | G | T | N | N | E |
| | | | | | | | | | 180 |
| Y | R | I | S | L | A | K | G | G |
| | | | | | | | | | 190 |
| G | C | P | V | M | N | L | H | A | E |
| | | | | | | | | | 200 |
| Y | T | T | S | F | E | S | F | I | D |
| | | | | | | | | | 210 |
| K | V | I | W | Y | N | F | Y | K | P |
| | | | | | | | | | 220 |
| I | V | Y | V | G | T | D | S | A | E |
| | | | | | | | | | 230 |
| E | E | E | I | L | L | E | V | S | L |
| | | | | | | | | | 240 |
| V | F | K | I | K | E | F | A | P | D |
| | | | | | | | | | 250 |
| A | P | L | Y | T | G | P | A | Y | | wherein G is glycine, A is alanine, V is valine, L is leucine, I is isoleucine, S is serine, T is threonine, D is aspartic acid, E is glutamic acid, N is asparagine, Q is glutamine, K is lysine, R is arginine, C is cysteine, M is methionine, F is phenylalanine, Y is tyrosine, W is tryptophan, H is histidine, and P is proline.

3. An isolated polyhedrin gene of *Spodoptera litura* nuclear polyhedrosis virus having the following base sequence:

|  10 |  20 |  30 |  40 |
|---|---|---|---|
| GATAAAATTT | TAAAATTTTA | ATCTATAGAT | AGAAAGATAA |
|  50 |  60 |  70 |  80 |
| AATTTTAATC | TATAGATAAA | AGTAAAGTAT | TTAGATAAAA |
|  90 | 100 | 110 | 120 |
| TTTTATCTAA | AAATTTTAAT | CTAAAGATAA | AATATTGACA |
| 130 | 140 | 150 | 160 |
| TGCGATTTCT | CAATACCAAT | GAAGATCAAG | TGATGATAAG |
| 170 | 180 | 190 | 200 |
| GAATTTATTA | CTATCGTTCT | AGATAGTGAA | AAATCAAATA |
| 210 | 220 | 230 | 240 |
| TCCCATAATG | TATAGTCGCT | ACAGTGCCTA | CAATTATAGT |
| 250 | 260 | 270 | 280 |
| CCCCATCTGG | GCAAAACCTA | TGTATACGAT | AACAAGTATT |
| 290 | 300 | 310 | 320 |
| ACAAAAATTT | AGGTCACGTG | ATCAAAAATG | CTAAGCGCAA |

-continued

| | | | |
|---|---|---|---|
| 330 | 340 | 350 | 360 |
| ACACGATGCT | CTCGAACGCG | AGGCCGACGA | GCGCGAGCTC |
| 370 | 380 | 390 | 400 |
| GATCACCTAG | ACAAGTATCT | AGTCGCCGAA | GATCCGTTCA |
| 410 | 420 | 430 | 440 |
| TGGGTCCCGG | TAAAAATCAA | AAGTTGACTC | TGTTCAAGGA |
| 450 | 460 | 470 | 480 |
| GATCCGTAAC | GTGAAACCCG | ACACGATGAA | GCTGATCGTC |
| 490 | 500 | 510 | 520 |
| AACTGGAACG | GCAAAGAGTT | TCTCCGTGAG | ACTTGGACCC |
| 530 | 540 | 550 | 560 |
| GTTTCATGGA | AGACAGCTTC | CCCATCGTGA | ACGATCAAGA |
| 570 | 580 | 590 | 600 |
| AGTGATGGAC | GTGTTTCTAG | TGGTGAACAT | GCGTCCCACT |
| 610 | 620 | 630 | 640 |
| AGACCGAACC | GTTGCTTTAG | ATTTTTGGCG | CAACACGCGC |
| 650 | 660 | 670 | 680 |
| TCCGATGCGA | CCCCGAGTAC | GTTCCCCACG | ACGTGATCCG |
| 690 | 700 | 710 | 720 |
| CATCGTCGAA | CCGTCGTACG | TCGGCACCAA | CAATGAATAC |
| 730 | 740 | 750 | 760 |
| CGCATCAGTC | TCGCCAAGAA | AGGTGGCGGT | TGTCCCGTGA |
| 770 | 780 | 790 | 800 |
| TGAACCTGCA | CGCCGAATAC | ACCACTTCGT | TTGAGAGTTT |
| 810 | 820 | 830 | 840 |
| CATCGACAAG | GTGATATGGT | ACAACTTTTA | CAAGCCCATC |
| 850 | 860 | 870 | 880 |
| GTGTACGTGG | GCACCGATTC | GGCCGAAGAG | GAGGAGATCC |
| 890 | 900 | 910 | 920 |
| TTCTCGAAGT | GTCGCTCGTG | TTCAAGATCA | AAGAGTTTGC |
| 930 | 940 | 950 | 960 |
| TCCCGACGCG | CCACTCTACA | CCGGTCCCGC | GTACTAAATT |
| 970 | 980 | 990 | 1000 |
| TGCGAAGAGG | ACAGTCGAGC | CAGTTCGTCG | ACTCTCCGTT |
| 1010 | 1020 | 1030 | 1040 |
| TGAGCTGTGC | AATTTTTTCG | TCGTCTTTGT | CGTCGCGACG |
| 1050 | 1060 | 1070 | 1080 |
| CTTCTGAAGC | ATACTTTTCG | CCTTTGCGAT | GTCATCGTTT |
| 1090 | 1100 | 1110 | 1120 |
| ACGATAAAGT | ATTCGACGGC | TCGCAAAAAT | CTCTCTCTGG |
| 1130 | 1140 | 1150 | 1160 |
| ACATTGTGTC | CGCTCGGTCG | CCGTTTGCCG | CCTCTTTGAC |
| 1170 | 1180 | 1190 | 1200 |
| CGCGCTCGGC | TCTGCGTCTT | TAAACATAAA | CTGAACAATA |
| 1210 | 1220 | 1230 | 1240 |
| GACATCGTCC | GTTCGACGCT | GTCAATGAGC | CGCAAAGCGT |
| 1250 | 1260 | 1270 | 1280 |
| CATCTTTCGC | AACGATATTT | TTTACATTGT | TTAAATCTCG |
| 1290 | ↑ 1300 | 1310 | 1320 |
| AAGTATATCG | GCCACGTTGC | TTTGTATAAT | TTGGCTGTTT |

4. A vector containing a polyhedrin gene of *Spodoptera litura* nuclear polyhedrosis virus, wherein at least part of said polyhedrin gene is replaced with a heterologous DNA sequence.

5. A vector containing a promoter of polyhedrin gene of *Spodoptera litura* nuclear polyhedrosis virus upstream from the 5' end of a heterologous DNA sequence and a fragment of the polyhedrin gene downstream from the 3' end of said heterologous DNA sequence.

6. A method of producing a vector, comprising:
 (a) cleaving the polyhedrin gene of *Spodoptera litura* nuclear polyhedrosis virus to produce a DNA fragment comprising a polyhedrin promoter and sufficient flanking DNA sequence to facilitate recombination;
 (b) inserting said DNA fragment into a cloning vehicle to obtain a modified cloning vehicle; and
 (c) inserting at least one heterologous DNA sequence into said modified vehicle so that the heterologous DNA sequence is under the transcriptional control of the polyhedrin promoter.

7. A recombinant *Spodoptera litura* nuclear polyhedrosis virus wherein at least a part of the polyhedrin gene is replaced with a heterologous DNA sequence.

8. A recombinant *Spodoptera litura* nuclear polyhedrosis virus containing a heterologous DNA sequence which is ligated downstream of a 5'-upstream polyhedrin promoter and which is ligated upstream of a 3'-downstream DNA fragment of a polyhedrin gene.

9. A method of producing a recombinant virus, comprising:
 (a) cleaving a polyhedrin gene of *Spodoptera litura* nuclear polyhedrosis virus to produce a DNA fragment comprising a polyhedrin promoter and sufficient flanking DNA sequence to facilitate recombination;
 (b) preparing a vector by inserting said DNA fragment into a cloning vehicle to obtain a modified cloning vehicle;
 (c) inserting at least one heterologous DNA sequence into said modified cloning vehicle so that the heterologous DNA sequence is under the transcriptional control of said polyhedrin promoter, to obtain a vector; and (d) contacting said vector with a virus (SlNPV C-411) so as to effect recombination.

10. Cells infected with the recombinant virus of claim 7.

11. Cells infected with the recombinant virus of claim 8.

12. A method for producing a polypeptide, which comprises culturing cells of claim 10.

13. A method for producing a polypeptide, which comprises culturing cells of claim 11.

14. A method of producing a polypeptide, which comprises:

(a) preparing a recombinant *Spodoptera litura* nuclear polyhedrosis virus wherein the DNA contains a heterologous DNA sequence which is ligated downstream of a 5'-upstream polyhedrin promoter and which is ligated upstream of a 3'-downstream DNA fragment of the polyhedrin gene; and (b) culturing a cell infected with said recombinant virus.

15. A recombinant gene, comprising a polyhedrin gene of the *Spodoptera litura* nuclear polyhedrosis virus SlNPV C-411, wherein at least part of said polyhedrin gene is replaced with a heterologous DNA sequence.

16. A recombinant gene, comprising a promoter of a polyhedrin gene of the *Spodoptera litura* nuclear polyhedrosis virus SlNPV C-411 5'-upstream from the 5' end of a heterologous DNA sequence and a fragment of said polyhedrin gene 3'-downstream from the 3' end of said heterologous DNA sequence.

* * * * *